(12) United States Patent
Leblond et al.

(10) Patent No.: US 8,835,463 B2
(45) Date of Patent: Sep. 16, 2014

(54) COMPOUNDS HAVING ANALGESIC AND/OR IMMUNOSTIMULANT ACTIVITY

(75) Inventors: Bertrand Leblond, Paris (FR); Eric Beausoleil, Paris (FR); Thierry Taverne, St. Martin Boulogne sur Mer (FR); John E. Donello, Dana Point, CA (US)

(73) Assignees: Allergan, Inc., Irvine, CA (US); Exonhit Therapeutics SA, Paris (FR)

( * ) Notice: Subject to any disclaimer, the term of this patent is extended or adjusted under 35 U.S.C. 154(b) by 226 days.

(21) Appl. No.: 13/409,853

(22) Filed: Mar. 1, 2012

(65) Prior Publication Data

US 2012/0157497 A1 Jun. 21, 2012

Related U.S. Application Data

(62) Division of application No. 11/814,593, filed as application No. PCT/US2006/002580 on Jan. 25, 2006, now Pat. No. 8,153,666.

(60) Provisional application No. 60/647,271, filed on Jan. 26, 2005.

(51) Int. Cl.
| | |
|---|---|
| A61K 31/4409 | (2006.01) |
| C07D 401/06 | (2006.01) |
| A61K 31/4025 | (2006.01) |
| C07D 319/18 | (2006.01) |
| A61K 31/4709 | (2006.01) |
| A61K 31/5377 | (2006.01) |
| C07D 213/64 | (2006.01) |
| A61K 31/4439 | (2006.01) |
| C07D 265/30 | (2006.01) |
| C07D 295/12 | (2006.01) |
| A61K 31/5375 | (2006.01) |
| A61K 31/541 | (2006.01) |
| A61K 31/4545 | (2006.01) |
| A61K 31/496 | (2006.01) |
| A61K 31/40 | (2006.01) |

(52) U.S. Cl.
CPC .......... *C07D 265/30* (2013.01); *A61K 31/4025* (2013.01); *C07D 319/18* (2013.01); *A61K 31/4709* (2013.01); *A61K 31/5377* (2013.01); *C07D 213/64* (2013.01); *A61K 31/4439* (2013.01); *C07D 295/12* (2013.01); *A61K 31/5375* (2013.01); *A61K 31/541* (2013.01); *A61K 31/4545* (2013.01); *A61K 31/496* (2013.01); *A61K 31/40* (2013.01); *A61K 31/4409* (2013.01)
USPC ............. 514/339; 546/268.1; 546/273.1; 514/336

(58) Field of Classification Search
CPC ..................... A61K 31/4409; C07D 401/06
USPC ............. 546/268.1, 273.1; 514/336, 339
See application file for complete search history.

(56) References Cited

U.S. PATENT DOCUMENTS

| | | | |
|---|---|---|---|
| 5,767,121 A | 6/1998 | Takatani et al. | |
| 5,916,911 A | 6/1999 | Shayman et al. | |
| 5,945,442 A | 8/1999 | Shayman et al. | |
| 5,952,370 A | 9/1999 | Shayman et al. | |
| 5,976,781 A | 11/1999 | Haldar et al. | |
| 6,030,995 A | 2/2000 | Shayman et al. | |
| 6,051,598 A | 4/2000 | Shayman et al. | |
| 6,407,064 B2 | 6/2002 | Masuda et al. | |
| 8,013,000 B2 | 9/2011 | Leblond et al. | |
| 8,153,666 B2 * | 4/2012 | Leblond et al. | 514/343 |
| 8,173,683 B2 * | 5/2012 | Donello et al. | 514/343 |
| 8,288,556 B2 * | 10/2012 | Leblond et al. | 546/279.1 |
| 2002/0198240 A1 | 12/2002 | Shayman et al. | |
| 2003/0050299 A1 | 3/2003 | Hirth et al. | |
| 2003/0153768 A1 | 8/2003 | Hirth | |

FOREIGN PATENT DOCUMENTS

| | | |
|---|---|---|
| EP | 0 720 852 | 7/1996 |
| EP | 0 765 865 | 4/1997 |
| EP | 782992 | 9/1997 |
| JP | 9-216858 | 8/1997 |
| JP | 10324671 | 12/1998 |
| WO | WO 95/05177 | 2/1995 |
| WO | WO 0104108 | 1/2001 |
| WO | WO 01/38228 | 5/2001 |
| WO | WO 01/47874 | 7/2001 |
| WO | WO 0212185 | 2/2002 |
| WO | WO 02062777 | 8/2002 |
| WO | WO 03008399 | 1/2003 |
| WO | WO 03045928 | 5/2003 |
| WO | WO 2005/063275 | 7/2005 |

OTHER PUBLICATIONS

Shin, S. et al, "Stereoselective synthesis of enantiomerically pure D-threo-PDMP; manipulation of a core 2,3-diamino alcohol unit", *Tetrahedron asymmetry*, 11, 3293-3301, 2000].

Kurosawa et al, "C-Labeling of a Novel Atypical β-Adrenoceptor Agonist, SLM-11044" Journal of Labelled Compounds & Radiopharmaceuticals (1996), 38(3).

Vunam, R. R. et al, "Analogs of ceramide that inhibit glucocerebroside synthetase in mouse brain", *Chem. Phys. Lipids*, 26, 265-278, 1980.

Mizutani A. et al, "Effects of Glucosylceramide Synthase Inhibitor and Ganglioside GQ1b on Synchronous Oscillations of Intracellular Ca2+ in Cultured Cortical Neurons", Biochem. Biophys. Res. Commun., 222, 494-498, 1996.

Abe, A. et al, "Structural and stereochemical studies of potent inhibitors of glucosylceramide synthase and tumor cell growth", *J. Lipid Res.* 36, 611-621, 1995.

Radin, A. et al, "Use of an Inhibitor of Glucosylceramide Synthesis, D-1-Phenyl-2-decanoylamino-3-morpholino-1-propanol", *NeuroProtocols*, 3(2), 145-55, 1993.

(Continued)

*Primary Examiner* — Golam M M Shameem
(74) *Attorney, Agent, or Firm* — Krishna Banerjee; Jonathan Bass

(57) ABSTRACT

The compounds shown by their structural formulas in the specification have analgesic and or immunostimulant activity in mammals.

3 Claims, No Drawings

(56) References Cited

OTHER PUBLICATIONS

Nishida, A., "Practical Synthesis of threo-(1S, 2S)- and erythro-(1R, 2S)-1-Phenyl-2-palmitoylamino-3-morpholino-1-propanol (PPMP) from L-Serine", *Synlett*, 4, 389-390, 1998.

Miura, T. et al, "Synthesis and Evaluation of Morpholino- and Pyrrolidinosphingolipids as Inhibitors of Glucosylceramide Synthatse", Bioorg. Med. Chem., 6, 1481-1498, 1998.

Mitchell et al, "Glycosyltransferase Inhibitors: Synthesis of D-threo-PDMP, L-threo-PDMP, and Other Brain Glucosylceramide Synthase Inhibitors from D- or L-Serine", *J. Org. Chem.*, 63 (24), 8837-8842, 1998.

Jimbo M. et al, "Development of a New Inhibitor of Glucosylceramide Synthase", *J. Biochem.*, 127(3) 485-91, 2000.

Lee, L. et al, "Improved Inhibitors of Glucosylceramide Synthase", *J. Biol. Chem.*, 274, 21, 14662-14669, 1999.

Kim et al, 1992, Pain 150, pp. 355-363.

Kastron et al. Latvijas PSR Zinatnu Akademijas Vestis, Kimijas Serija (1965) (4), 471-7.

Inokuchi, J. et al, "Preparation of the active isomer of 1-phenyl-2-decanoylamino-3-morpholino-1-propanol, inhibitor of murine glucocerebroside", *J. Lipid Res.* 28, 565-571, 1987.

Inokuchi et al, "A Synthetic Ceramide Analog (L-PDMP) Up-regulates Neuronal Function", *Ann. N.Y. Acad. Sci.*, 845(1), 219-224, 1998.

Inokuchi J. et al, "Antitumor Activity Via Inhibition of Glycosphingolipid Biosynthesis", *Cancer Letters* 38(1-2), 23-30, 1987.

Husain A. et al, "syn-Selective additions to Garner aldehyde: synthesis of a potent glucosylceramide synthase inhibitor", *Tetrahedron Lett.*, 43, 8621-8623, 2002.

Dixon, W.J., *Ann. Rev. Pharmacol. Toxicol.* 20:441-462 (1980).

Abe, A. et al., "Improved Inhibitors of Glucosylceramide Synthase", *J. Biochem.*, 111, 191-196, 1992.

Slavish., J. P. et al, "New PDMP analogues inhibit process outgrowth in an insect cell line", Bioorg. Med. Chem. Lett., 14, 1487-1490, 2004.

Bixler, Robert et al, Synthesis of β-(4-Pyridyl)-DL-Alanine and of β-(4-Pyridyl-l-oxide)-DL-, D-, and L-Alanine, Journal of Organic Chemistry, Apr. 1958, 575-584, 23.

Burford, Hugh et al, Pharmacological Studies on Some New Acrylic Acid Amide Derivatives, Journal of Pharmaceutical Sciences, Dec. 1965, 1750-1754, 54(12).

Gregory, H. et al., Polypeptides. Part VII. Variations of the Phenylalanyl Position in the C-Terminal Tetrapeptide Amide Sequence of the Gastrins, Journal of the Chemical Society, 1968, pp. 531-540.

Inokuchi et al., Amino Alcohol esters as ceramide analogs and pharmaceuticals containing them for treatment of nerve diseases, XP002381282, 1998, 1 pg.

Tabanella et al., Preparation of Enantiomerically Pure Pyridyl Amino Acids from Serine, Organic & Biomolecular Chemistry, 2003, 4254-4261, vol. 1, No. 23.

Tucker et al., a Series of Potent HIV-1 Protease Inhibitors Containing a Hydroxyethyl Secondary Amine Transitiion State Isostere: Synthesis; Enzyme Inhibition, and Antiviral Activity, 1992, Journal of Medicinal Chemistry, 35 (14) 2525-33, 14.

Venturella et al., Synthesis of Several Derivatives of Phenyl(2-hdroxy-3-yrazyl)carbinol, Feb. 1963, Journal of Pharmaceutical Sciences, vol. 52, No. 2, 142-146.

Vlasenko et al., Study of Anesthetic Properties of Beta Amino Alcohols, 1975, XP00806641, pp. 18-20, vol. 28, No. 11, US.

* cited by examiner

COMPOUNDS HAVING ANALGESIC AND/OR IMMUNOSTIMULANT ACTIVITY

CROSS REFERENCE TO RELATED APPLICATIONS

This application is a divisional of U.S. patent application Ser. No. 11/814,593, filed Sep. 10, 2009, now U.S. Pat. No. 8,153,666 which is a national stage application under 35 U.S.C. §371 of PCT application PCT/US2006/002580, filed on Jan. 25, 2006, and claims the benefit U.S. Provisional Application No. 60/647,271, filed on Jan. 26, 2005, all of which are incorporated herein by reference in their entirety.

BACKGROUND OF THE INVENTION

1. Field of the Invention

The present invention relates to compounds having analgesic and in some cases immunostimulant activity.

The present invention also relates to pharmaceutical compositions containing these compounds as active ingredient for alleviating or eliminating pain in mammals and/or stimulating the immune system in mammals and to methods of using said pharmaceutical compositions as analgesics and or immunostimulants.

2. Background Art

Several compounds falling within one or more of the general definitions as "derivatives of 3-aryl-3-hydroxy-2-aminopropionic acid amides, of 3-heteroaryl-3-hydroxy-2-aminopropionic acid amides, of 1-aryl-1-hydroxy-2,3-diaminopropyl amines, 1-heteroaryl-1-hydroxy-2,3-diamino-propyl amines" are known in the patent and scientific literature.

For example, United States Patent Application Publications US 2003/0153768; US 2003/0050299 disclose several examples of the above-mentioned known compounds. The N-acyl compounds of these references are said to be useful as N-acylsphingosine glucosyltransferase inhibitors, the amide and the reduced compounds are described as intermediates in their preparations.

Illustrative specific examples of compounds of these references are shown below:

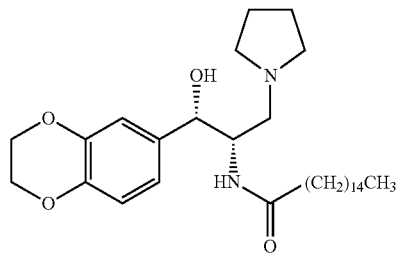

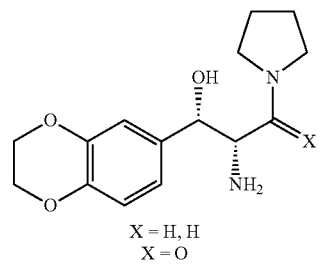

X = H, H
X = O

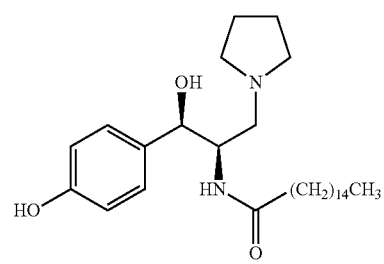

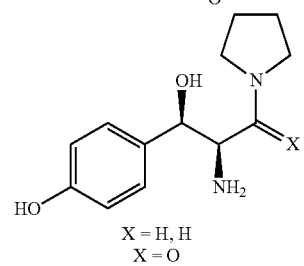

X = H, H
X = O

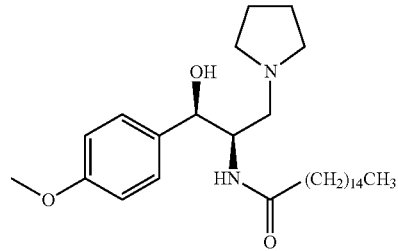

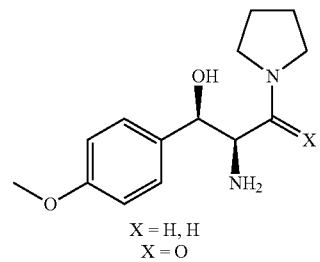

X = H, H
X = O

The publication Shin et al. *Tetrahedron Asymmetry*, 2000, 11, 3293-3301 discloses the following compounds:

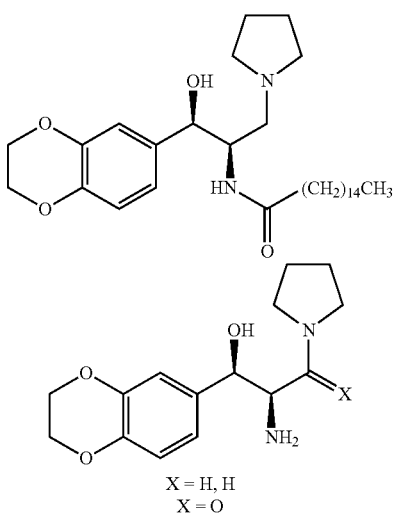

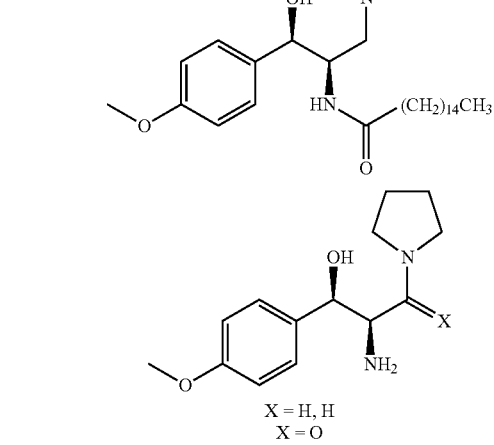

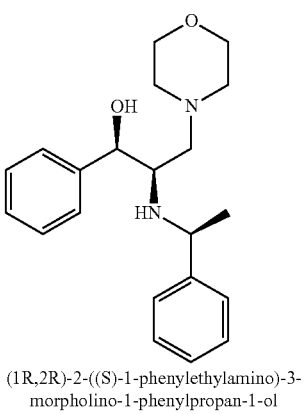

(1R,2R)-2-((S)-1-phenylethylamino)-3-morpholino-1-phenylpropan-1-ol

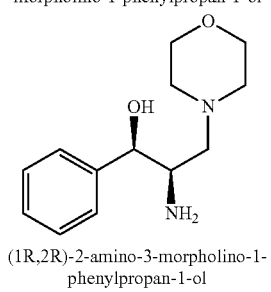

(1R,2R)-2-amino-3-morpholino-1-phenylpropan-1-ol

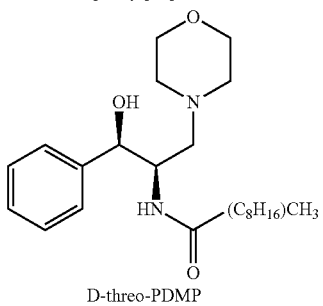

D-threo-PDMP

L-threo-PDMP and some other known compounds used in the methods of this invention are commercially available, in pure enantiomeric and racemic forms, as applicable, from Matreya, LLC Pleasant Gap, Pa.

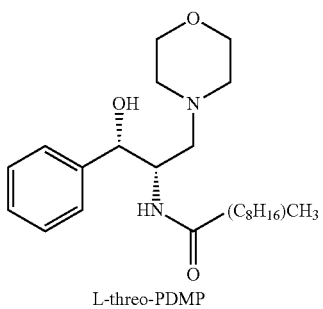

L-threo-PDMP

U.S. Pat. Nos. 5,945,442; 5,952,370; 6,030,995 and 6,051,598, which are all related to each other as being based on same or related disclosures, describe compounds which are structurally similar to the known compounds shown above. The compounds of these U.S. patent references are said to be inhibitors of the enzyme glucosylceramide (GlcCer) synthethase.

A publication in Journal of Labelled Compounds & Radiopharmaceuticals (1996), 38(3), 285-97 discloses the compound of the formula

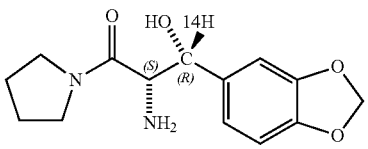

Published PCT application WO 01/38228 discloses

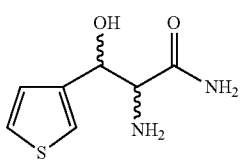 [SMILES: NC(=O)C(N)C(O)c1ccsc1]

in connection with a chromatographic method.

Kastron et al. in Latvijas PSR Zinatnu Akademijas Vestis, Kimijas Serija (1965) (4), 474-7 disclose the following compound.

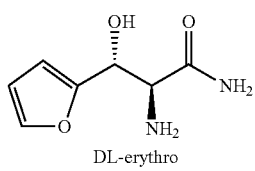 [SMILES: NC(=O)[C@@H](N)[C@@H](O)c1ccco1]

DL-erythro

Significantly, according to the best knowledge of the present inventors none of the above shown prior art compounds are disclosed in the prior art to have analgesics or immunostimulants activity.

SUMMARY OF THE INVENTION

The present invention is directed to novel compounds shown by their structural formulas below:

COMPOUND 19

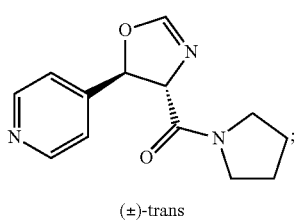

(±)-trans

COMPOUND 50
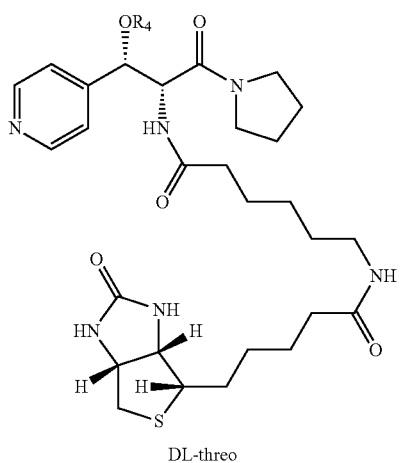
DL-threo
where $R_4$ is H, alkyl of 1 to 6 carbons or CO—$R_5$ where $R_5$ is alkyl of 1 to 6 carbons;
COMPOUND 70
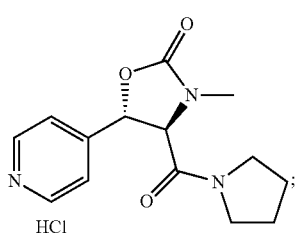
(±)
Compound 49
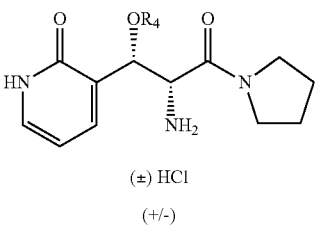
(±) HCl
(+/−)
where $R_4$ is H, alkyl of 1 to 6 carbons or CO—$R_5$ where $R_5$ is alkyl of 1 to 6 carbons;
Compound 300
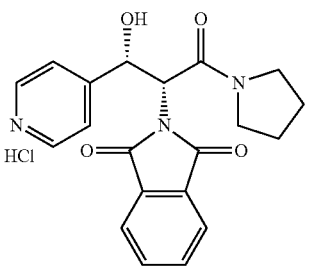
(±)
where $R_4$ is H, alkyl of 1 to 6 carbons or CO—$R_5$ where $R_5$ is alkyl of 1 to 6 carbons;
Compound 301
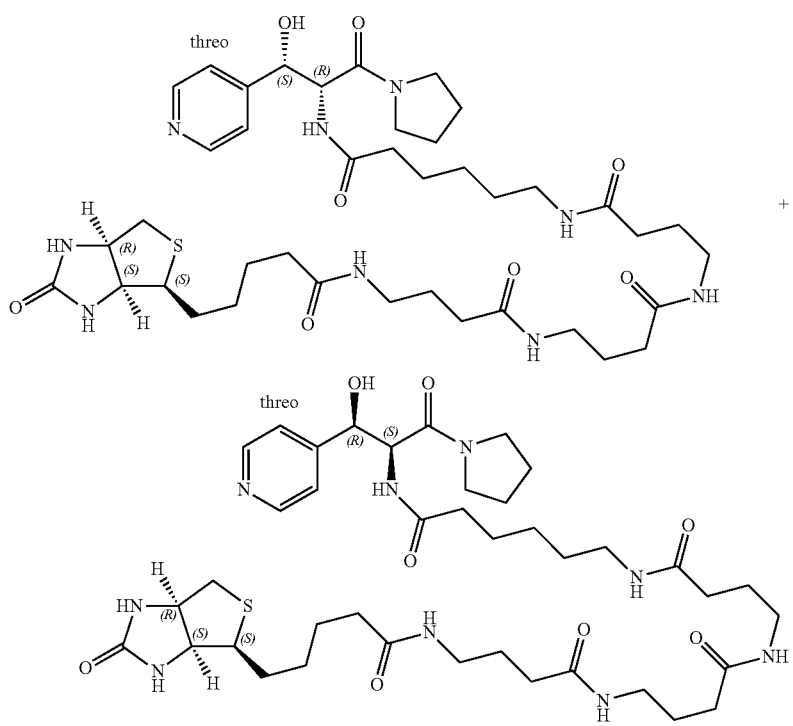

where $R_4$ is H, alkyl of 1 to 6 carbons or CO—$R_5$ where $R_5$ is alkyl of 1 to 6 carbons;

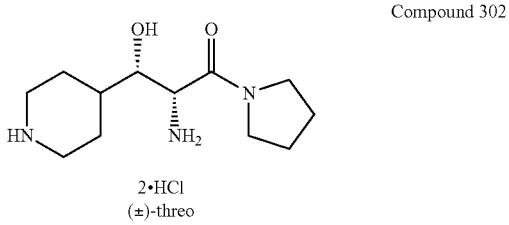 [SMILES: N[C@@H](C(=O)N1CCCC1)[C@@H](O)C1CCNCC1]

Compound 302

2·HCl
(±)-threo where $R_4$ is H, alkyl of 1 to 6 carbons or CO—$R_5$ where $R_5$ is alkyl of 1 to 6 carbons, and to all pharmaceutically acceptable salts of said compounds.

The present invention is also directed to pharmaceutical compositions containing the above-noted novel compound to be used as analgesics and/or immunostimulants in mammals and to methods of using said pharmaceutical compositions as analgesics and/or as immunostimulants.

DETAILED DESCRIPTION OF THE INVENTION

A general description of the compounds of the invention is provided in the Summary Section of the present application for patent. Several compounds of the invention contain one or more asymmetric centers, such that the compounds may exist in enantiomeric as well as in diastereomeric forms. In fact, most of the compounds of the present invention have two asymmetric carbons adjacent to one another and therefore can exist in erythro or threo form, with each of these two forms having dextrorotatory (D) or levorotary (L) enantiomers. Although the threo form is generally preferred in accordance with the present invention for analgesic activity, unless it is specifically noted otherwise, the scope of the present invention includes all enantiomers, diastereomers and diastereomeric and racemic mixtures. In light of the foregoing, it should be clearly understood that the designation "DL" or "(+/−)" or "(±)" in this application includes the pure dextrorotatory enantiomer, the pure levorotatory enantiomer and all racemic mixtures, including mixtures where the two enantiomers are present in equal or in unequal proportions. Moreover, for simplicity sake in many of the structural formulas, such as in the example below, only one of the enantiomers is actually shown but when the designation "DL" (or "(+/−)" or "(±)") appears it also includes the enantiomeric form (mirror image) of the structure actually shown in the formula.

For Example:

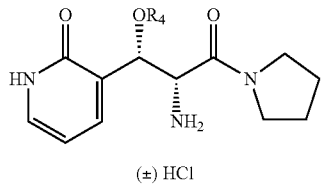

(±) HCl

Thus, in the example above, only one enantiomer is shown, but because the designation "DL" (or "(+/−)" or "(±)") appears below the formula, its optical isomer

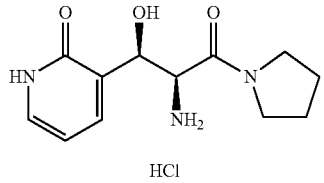 [SMILES: N[C@H](C(=O)N1CCCC1)[C@H](O)c1ccc[nH]c1=O ; Cl]

HCl and all racemic mixtures of the two optical isomers are also included.

In the case of some compounds of the present invention one enantiomer of the threo, and in some cases of the erythro, is significantly more active as an analgesic or immunostimulant than the other enantiomer of the same pair. For this reason the isolated enantiomer which is significantly more active than the other is considered a novel and inventive composition even if the racemic mixture or one single enantiomer of the same compounds have already been described in the prior art.

Some of the novel compounds of the present invention may contain three or more asymmetric centers.

Keeping the foregoing examples in mind a person of ordinary skill in the art should readily understand the scope of each described example, although in a broad sense all isomers, enantiomers and racemic mixtures are within the scope of the invention.

The term "alkyl" in the general description and definition of the compounds includes straight chain as well as branch-chained alkyl groups.

Generally speaking the compounds of the invention may form salts with pharmaceutically acceptable acids or bases, and such pharmaceutically acceptable salts of the compounds are also within the scope of the invention.

Referring now to the novel compounds of the invention the $R_4$ group shown above and in the claims, is preferably H.

The presently most preferred novel compounds of the invention are disclosed with their structural formulas in the ensuing Table and or description, showing activity of exemplary compounds relevant to their ability to act as analgesics.

Biological Activity, Modes of Administration

The novel compounds of the invention have analgesic and/or immunostimulant activity in mammals. Some of the compounds described in the introductory section which per se are known in the art have been discovered by the present inventors to also have analgesic effect in mammals. To the best of the knowledge of the present inventors the analgesic or immunostimulant biological activity of the known compounds was not known before the present discovery.

An art-accepted model or assay for measuring an analgesic effect of a compound in chronic pain (in particular peripheral neuropathy) is the model known as Kim and Chung 1992, Pain 150, pp 355-363 (Chung model). This model involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to low-threshold mechanical stimuli and will perceive pain instead of the faint sensation of touch. This sensitivity to normally non-painful touch, called "tactile allodynia", develops within the first week after surgery and lasts for at least two months. The allodynia response includes lifting the affected hindpaw to escape from the stimulus, licking the paw and holding it in the air for many seconds. None of these responses is normally seen in the control group.

To produce the tactile allodynia, rats are anesthetized before surgery. The surgical site is shaved and prepared either with betadine or Novacaine. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

After a complete hemostasis is confirmed, the wounds are sutured. A small amount of antibiotic ointment is applied to the incised area, and the rat is transferred to the recovery plastic cage under a regulated heat-temperature lamp.

On the day of the experiment, at least seven days after the surgery, typically six rats per test group are administered the test drugs by intraperitoneal (i.p.) injection or oral gavage (p.o.). For i.p. administration, the compounds are formulated in $H_2O$ and given in a volume of 1 ml/kg body weight by injecting into the intraperitoneal cavity. For p.o. administration, the compounds are formulated in $H_2O$ and given in a volume of 1 ml/kg body weight using an 18-gauge, 3 inch gavage needle that is slowly inserted through the esophagus into the stomach.

Tactile allodynia is assessed via von Frey hairs, which are a series of fine hairs with incremental differences in stiffness. Rats are placed in a plastic cage with a wire mesh bottom and allowed to acclimate for approximately 30 minutes. To establish the pre-drug baseline, the von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980) hereby incorporated by reference. Tactile allodynia is measured prior to and 15, 30, and 60 minutes after drug administration. The post-drug threshold is compared to the pre-drug threshold and the percent reversal of tactile sensitivity is calculated based on a normal threshold of 15.1 grams.

Table 1 below indicates the degree of pain reversal obtained in the Chung model with exemplary compounds of the invention. The intraperitonial (i.p.) and/or intravenous (iv) administration of the compounds was in doses ranging from 1 μg/kg to 300 μg/kg or 3 mg/kg PO and the peak percentage of reversal of allodynia was measured at 15, 30 or 60 minutes after administration, as is indicated in the table. Data are expressed as the highest % allodynia reversal (out of 3 time points: 15 min, 30 min, or 60 min. post-drug) with a minimum of a 20% allodynia reversal in the rat Chung model. Comparisons between groups (drug treated vs. saline treated) were made using a two-tailed, 2-sample, unpaired t-test. Compounds that are not shown which were not statistically analgesic following an IP dose of 300 ug/kg, but may still be analgesic. Compounds that do not exhibit significant analgesia at 100 mg/kg are not considered to be analgesic.

TABLE 1

| Compound # | Chemical Formula | Peak % Pain Reversal: time post dose | Dose μg/kg Mode of Admi Nistr. |
|---|---|---|---|
| 19 | (±)-trans | 43% 30 min | 300 μg/kg IP |
| 50 | threo + threo / threo | 100% 60 min | 300 μg/kg PO |

TABLE 1-continued

| Compound # | Chemical Formula | Peak % Pain Reversal: time post dose | Dose μg/kg Mode of Administr. |
|---|---|---|---|
| 70 | 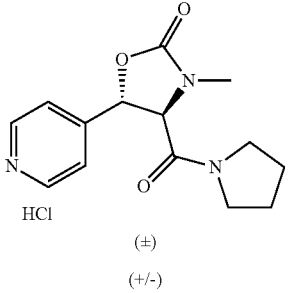 [SMILES: CN1C(=O)O[C@@H](c2ccncc2)[C@@H]1C(=O)N1CCCC1 ; Cl] | 69% 60 min | 300 μg/kg IP |
| 49 | 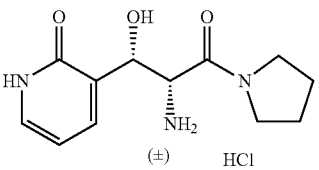 [SMILES: N[C@@H](C(=O)N1CCCC1)[C@@H](O)c1ccc[nH]c1=O ; Cl] | 85% 60 min | 100 μg/kg IP |
| 300 | 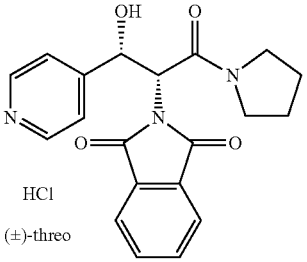 [SMILES: O=C([C@@H]([C@@H](O)c1ccncc1)N1C(=O)c2ccccc2C1=O)N1CCCC1 ; Cl] | 53% 60 min | 300 μg/kg IP |

An art accepted method for measuring immunostimulation comprises systemic administration of compounds to assay for the ability to stimulate the immune system, possibly due to nonspecific upregulation of the hemolymphoreticular system. This upregulation could result in increased numbers of lymphocytes of both T- and B-cell lineage. Although applicant does not wish to be bound by the biological theory of the immunostimulation, actual immunostimulatory efficacy of the compounds can be demonstrated in vivo by assaying splenic size in response to administration of the test compound to laboratory test species rats. Thus, increase in spleen size demonstrates immunostimulatory potential of the compound. Generally speaking any compound that exhibits splenic enlargement following dosing of 200 mg/kg or less may be considered an immunostimulant.

Modes of Administration:

The compounds of the invention may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. For human adults such doses generally will be in the range 0.1-5000 mg/day; more preferably in the range 1 to 3000 mg/day, still more preferably in the range of 10 mg to 1000 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, intraperitonial, parenteral, subcutaneous, intranasal, intrathecal, intramuscular, intravenous and intrarectal modes of delivery. Another aspect of the invention is drawn to therapeutic compositions comprising the novel compounds of the invention and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as an excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

In another aspect, the invention is directed to methods for the treatment of pain, particularly chronic pain, through the administration of one or more of the novel or otherwise known compounds of the invention, or of pharmaceutically acceptable salts thereof to a mammal in need thereof. As indicated above, the compound will usually be formulated in a form consistent with the desired mode of delivery.

Compounds of the invention which are immunostimulants are administered subject to the same basic principles as the compounds having analgesic activity, in doses which are best determined on a case-by-case and/or species-by-species and, in case of humans, at times on a patient-by-patient basis. Generally speaking the effective dose will be in the range of 10 µg/kg to 200 mg/kg.

Synthetic Methods for Obtaining the Compounds of the Invention

The compound of the invention can be synthesized by utilizing the synthetic methods described in the experimental below, or such modifications of the below described experimental methods which will become readily apparent to those skilled in the art in light of the present disclosure. More specifically, the synthesis of each compound of the invention is described for the specific compounds wherein the variable $R_4$ is H. It will be readily understood by those skilled in the art that the compounds wherein the variable $R_4$ is alkyl of 1 to 6 carbons or CO—$R_5$ where $R_5$ is alkyl of 1 to 6 carbons can be readily made by processes well known in the art, such as alkylation or acylation, respectively. It will also be readily understood by those skilled in the art that for the performance of the alkylation or acylation of the hydroxyl group other groups, such as the amino group, may need to be protected and the protective group can be subsequently removed by processes well known in the art. In some cases the alkylation or acylation of the hydroxyl group may be performed on an intermediate in the synthetic process leading to the compounds of the invention.

General $^1$H NMR spectra were recorded at ambient temperature with an Avance 300 (Bruker) spectrometer. The compounds were analyzed by reverse phase high performance liquid chromatography (HPLC) using a Waters Autopurification System equipped with a Waters 2525 Pump, a Waters 2696 photodiode array detector, and a XTerra column (Part. No. 186000482, 5 µm, C18, 4.5×50 mm).

The HPLC method used was a gradient of 5% solvent B to 100% in 7 min. Solvent A was $H_2O$ with 0.05% TFA and solvent B was $CH_3CN$ with 0.05% TFA (Method A). Melting points were measured with a Büchi B-545 melting point apparatus and were uncorrected. To isolate reaction products the solvent were removed by evaporation using a vacuum rotatory evaporator, the water bath temperature not exceeding 40° C.

General Synthetic Routes

The compound of the invention can be synthesized by utilizing the synthetic methods described in a general sense immediately below and in more detail in the experimental section of the present application, or by such modifications of the below described general and experimental methods which will become readily apparent to those skilled in the art in light of the present disclosure.

Detailed Description of the Synthesis of Preferred Compounds (Experimental)

Preparation of Compound 19.

2-lsocyano-1-(pyrrolidin-1-yl)ethanone BLE 04098

To stirred and cooled (0° C.) methyl isocyanoacetate (96% technical grade, 5.0 g, 47.8 mmol) was slowly added in 0.75 h pyrrolidine (6.5 mL, 78 mmol). The mixture was stirred for 1.5 h with continued cooling and then concentrated. The resulting oil was co-evaporated twice from $CH_2Cl_2$:hexane to remove residual pyrrolidine. 2-lsocyano-1-(pyrrolidin-1-yl) ethanone BLE 04098 was obtained as a yellow solid (6.85 g, 98% yield) and used in the next step without purification.

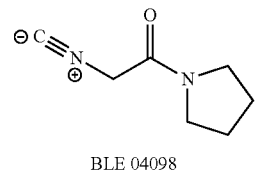

BLE 04098

MW: 138.17; Yield: 98%; yellow solid; Mp (° C.)=73.9.

$^1$H-NMR (CDCl$_3$,.): 1.81-2.08 (m, 4H, 2×CH$_2$), 3.35-3.45 (m, 2H, N—CH$_2$), 3.50-3.60 (m, 2H, N—CH$_2$), 4.23 (s, 2H, CH$_2$CO).

General Method B: Exemplified by the Preparation of trans-(4,5-dihydro-5-(pyridin-3-yl)oxazol-4-yl) (pyrrolidin-1-yl)methanone BLE 04110B To a stirred and cooled (0° C.) solution of potassium hydroxide (0.55 g, 9.80 mmol) in methanol (10 mL) were added a mixture of 3-pyridine carboxaldehyde (1.03 mL, 10.84 mmol) and 2-isocyano-1-(pyrrolidin-1-yl)ethanone BLE 04098 (1.50 g, 10.86 mmol). The solution was stirred 3 h at 0° C. and then concentrated. The residue was partitioned between ethyl acetate (100 mL) and water. The organic layer was combined with two additional ethyl acetate extracts (2×100 mL), washed with aqueous sodium chloride and dried over MgSO$_4$, filtered and evaporated. Concentration afforded a crude product which was purified by column chromatography on silica (CH$_2$Cl$_2$:MeOH=98:2) to yield to trans-(4,5-dihydro-5-(pyridin-3-yl)oxazol-4-yl)(pyrrolidin-1-yl) methanone BLE 04110B (0.95 g, 39%) as a pale yellow pale solid.

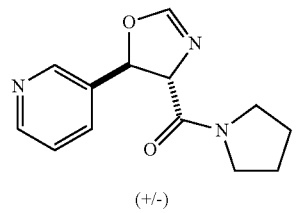

(+/−)

BLE 04110B

MW: 245.28; Yield: 39%; Yellow Pale Solid; Mp (° C.): 107.0.

$^1$H-NMR (CDCl$_3$,.): 1.78-2.10 (m, 4H, 2×CH$_2$), 3.40-3.61 (m, 3H, CH$_2$N), 3.90-4.04 (m, 1H, CH$_2$N), 4.59 (dd, 1H, J=7.7 Hz, J=2.2 Hz, CH—N), 6.21 (d, 1H, J=7.7 Hz, CH—O), 7.04 (d, 1H, J=2.2 Hz, O—CH=N), 7.33 (m, 1H, ArH), 7.64 (m, 1H, ArH), 8.59 (d, 2H, J=2.8 Hz, ArH).

$^{13}$C-NMR (CDCl$_3$,.): 24.2, 26.0, 46.4, 46.6, 75.7, 79.3, 123.7, 133.5, 135.3, 147.6, 149.9, 155.2, 166.2.

trans-(4,5-Dihydro-5-(pyridin-4-yl)oxazol-4-yl)(pyrrolidin-1-yl)methanone Compound 19

Compound 19 was prepared in accordance with method B using pyridine-4-carbaldehyde (1.88 mL, 19.76 mmol), KOH (1.01 g, 18.00 mmol) in methanol (18 mL) and 2-isocyano-1-(pyrrolidin-1-yl)ethanone BLE 04098 (2.73 g, 19.76 mmol). The residue was partitioned between ethyl acetate (200 mL) and water (150 mL). The organic layer was combined with additional ethyl acetate extracts (2×150 mL), washed with aqueous sodium chloride (2×150 mL) and dried over MgSO$_4$, filtered and evaporated. Trans-(4,5-dihydro-5-(pyridin-4-yl)oxazol-4-yl)(pyrrolidin-1-yl)methanone Compound 19 was obtained as a white solid (4.32 g, 98% yield).

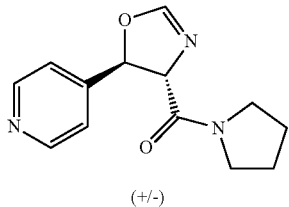

Compound 19

(+/-)

MW: 245.28; Yield: 98%; White Solid; Mp (° C.)=69.2. R$_f$: 0.65 (MeOH:CH$_2$Cl$_2$=10:90).
$^1$H-NMR (CDCl$_3$,.): 1.78-2.06 (m, 4H, 2×CH$_2$), 3.44-3.60 (m, 3H, CH$_2$N), 3.90-4.01 (m, 1H, CH$_2$N), 4.52 (dd, 1H, J=7.9 Hz, J=2.2 Hz, CH—N), 6.19 (d, J=7.9 Hz, 1H, CH—O), 7.03 (d, 1H, J=2.2 Hz, N=CH—O), 7.24 (dd, 2H, J=4.5 Hz, J=1.5 Hz, ArH), 8.61 (dd, 2H, J=4.5 Hz, J=1.5 Hz, ArH).

Preparation of Compound 50.

General Method C: Exemplified by the Preparation of DL-threo-2-amino-3-hydroxy-3-(pyridin-3-yl)-1-(pyrrolidin-1-yl)propan-1-one dihydrochloride Compound 20

To a solution of trans-(4,5-dihydro-5-(pyridin-3-yl)oxazol-4-yl)(pyrrolidin-1-yl)methanone BLE 04110B (0.932 g, 3.80 mmol) in MeOH (10 mL) was added hydrochloric acid 37% (1.2 mL). After heating (50° C.) the mixture for 2.25 h the reaction mixture was concentrated and the crude product was coevaporated twice with ethyl acetate. After trituration with ethyl acetate, filtration and drying DL-threo-2-amino-3-hydroxy-3-(pyridin-3-yl)-1-(pyrrolidin-1-yl)propan-1-one dihydrochloride Compound 20 was obtained as a white solid (1.10 g, 94% yield).

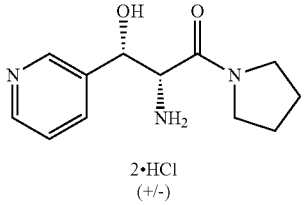

Compound 20

2•HCl
(+/-)

MW: 308.2; Yield: 94%; White Solid; Mp (° C.): 123.4.
$^1$H-NMR (CD$_3$OD,.): 1.65-2.00 (m, 4H, 2×CH$_2$), 2.82-3.11 (m, 1H, —CH$_2$N), 3.30-3.57 (m, 2H, C$_2$HN), 3.57-3.77 (m, 1H, CH$_2$N), 4.54 (d, 1H, J=5.3 Hz, CH—N), 5.38 (d, 1H, J=5.3 Hz, CH—O), 8.15 (dd, 1H, J=7.6 Hz, J=5.0 Hz, ArH), 8.68 (d, 1H, J=7.6 Hz, ArH), 8.89 (d, 1H, J=7.6 Hz, ArH), 8.96 (s, 1H, ArH).
$^{13}$C-NMR (CD$_3$OD,.): 24.9, 26.9, 47.7, 48.2, 58.1, 69.6, 128.7, 141.5, 141.6, 143.1, 146.5, 165.4.

DL-threo-2-Amino-3-hydroxy-3-(pyridin-4-yl)-1-(pyrrolidin-1-yl)propan-1-one dihydrochloride Compound 22

Compound 22 was prepared following method C with trans-(4,5-dihydro-5-(pyridin-4-yl)oxazol-4-yl)(pyrrolidin-1-yl)methanone Compound 19 (0.750 g, 3.07 mmol), hydrochloric acid 37% (1.0 mL) and methanol (10 mL). After 3.0 h at 50° C. and work-up DL-threo-2-amino-3-hydroxy-3-(pyridin-4-yl)-1-(pyrrolidin-1-yl)propan-1-one dihydrochloride Compound 22 was obtained as a white solid (0.935 g, 99% yield).

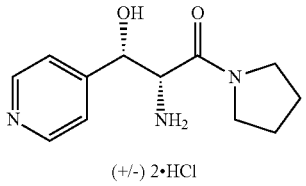

Compound 22

(+/-) 2•HCl

MW: 308.28; Yield: 99%; White Solid; Mp (° C.): 117.0.
$^1$H-NMR (CD$_3$OD,.): 1.75-2.03 (m, 4H, 2×CH$_2$), 2.93-3.08 (m, 1H, CH—N), 3.32-3.75 (m, 3H, 2×CH$_2$), 4.54 (d, 1H, J=5.9 Hz, CH—N), 5.40 (d, 1H, J=5.9 Hz, CH—O), 8.21 (d, 2H, J=5.8 Hz, ArH), 8.94 (d, 2H, J=5.8 Hz, ArH).
MS-ESI m/z (% rel. int.): 236.1 ([MH]$^+$, 17), 219 (25), 148 (100).
HPLC: Method A, detection UV 254 nm, Compound 22 RT=0.8 min, peak area 96.3%.

tert-Butyl 5-(DL-threo-1-hydroxy-3-oxo-1-(pyridin-4-yl)-3-(pyrrolidin-1-yl)propan-2-ylcarbamoyl)pentylcarbamate EBE 06102

To a suspension of DL-threo-2-amino-3-hydroxy-3-(pyridin-4-yl)-1-(pyrrolidin-1-yl)propan-1-one dihydrochloride Compound 22 (0.60 g, 1.77 mmol) in CH$_2$Cl$_2$ (12 mL) was added TEA (0.739 mL, 5.32 mmol) and the reaction mixture was stirred for 10 min and cooled in an ice bath with continuous stirring. A solution of Boc-aminohexanoic acid (0.451 g, 1.951 mmol) and BOP (1.05 g, 1.95 mmol) was pre-prepared in CH$_2$Cl$_2$ and added dropwise for 5 min. The reaction mixture was stirred for 2 h at 0° C. and 16 h at RT. After evaporation of the volatiles, the residue was dissolved in EtOAc, washed with NaH$_2$PO$_4$ pH 7.2, saturated NaHCO$_3$, dried over Na$_2$SO$_4$. The resulting white solid was purified by column chromatography on silica gel with 10% EtOAc in EtOAc to give tert-butyl 5-(DL-threo-1-hydroxy-3-oxo-1-(pyridin-4-yl)-3-(pyrrolidin-1-yl)propan-2-ylcarbamoyl)pentylcarbamate EBE 06102 (0.41 g, 52% yield) as a white solid.

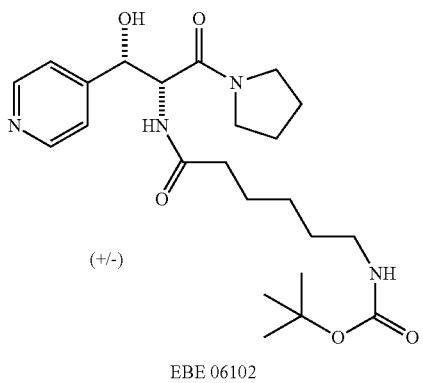 [SMILES: CC(C)(C)OC(=O)NCCCCCC(=O)N[C@@H](C(=O)N1CCCC1)[C@@H](O)c1ccncc1]

EBE 06102 (+/-)

MW: 448.56; Yield: 52.0%; White Solid.

$R_f$: 0.10 (EtOAc:MeOH=90:10).

$^1$H-NMR: (CDCl$_3$,.): 1.10-1.12 (m, 2H, CH$_2$), 1.35-1.55 (m, 11H, (CH$_3$)$_3$ & CH$_2$), 1.72-1.92 (m, 4H, CH$_2$), 2.05-2.22 (m, 2H, CH$_2$), 2.40 (d, 2H, J=9.3 Hz, CH$_2$), 3.05 (q, 2H, J=6.6 Hz, CH$_2$), 3.20-3.28 (m, 1H, NCH$_2$), 3.32-3.50 (m, 2H, NCH$_2$), 3.62-3.72 (m, 1H, NCH$_2$), 4.79 (bs, 1H, NH), 4.97 (dd, 1H, J=8.7, 4.1 Hz, NCH), 5.07 (d, 1H, J=4.1 Hz, OCH), 5.40 (bs, 1H, NH), 6.74 (d, 1H, J=8.4 Hz, OH), 7.35 (d, 2H, J=6.0 Hz, ArH), 8.56 (d, 2H, J=6.0 Hz, ArH).

$^{13}$C-NMR (CDCl$_3$,.): 24.0, 25.0, 26.1, 28.4, 29.6, 35.9, 36.9, 40.3, 46.1, 46.9, 54.9, 72.9, 79.0, 121.3, 148.8, 149.6, 156.1, 169.0, 173.2.

MS-ESI m/z (% rel. Int.): 449.1 ([MH]$^+$, 20).

HPLC: Method A, detection UV 254 nm, EBE 06102 RT=4.1 min, peak area 99.9%.

6-(5-((3aR,6S,6aS)-hexahydro-2-oxo-1H-thieno[3,4-d]imidazol-6-yl)pentanamido)-N-((1R,2S)- & (1S,2R)-1-hydroxy-3-oxo-1-(pyridin-4-yl)-3-(pyrrolidin-1-yl)propan-2-yl)hexanamides Compound 50

To a solution of 5-(DL-threo-1-hydroxy-3-oxo-1-(pyridin-4-yl)-3-(pyrrolidin-1-yl)propan-2-ylcarbamoyl)pentylcarbamate EBE 06102 (0.370 g, 0.824 mmol), in MeOH (1 mL) was added a solution of HCl (4.2 M) in EtOAc (10 mL). The reaction mixture was stirred for 2 h at RT and the volatiles were evaporated to yield a crude brown oil EBE 06104 (0.221 g, 63% crude yield) that was used without purification in the next step. To a suspension of EBE 06104 (0.221 g, 0.522 mmol) in CH$_2$Cl$_2$ (5 mL) was added triethylamine (0.217 mL, 1.57 mmol) and the reaction mixture was stirred for 10 min and cooled in an ice bath with continuous stirring. A solution of biotin (0.14 g, 0.574 mmol) and BOP (0.309 g, 0.574 mmol) was pre-prepared in CH$_2$Cl$_2$ (1 mL) and added dropwise for 5 min. The mixture was stirred for 2 h at 0° C. and 16 h at RT. The reaction mixture was evaporated to dryness, partitioned between NaH$_2$PO$_4$ and n-Butanol. The n-butanol phase was washed with saturated Na$_2$CO$_3$ and evaporated to dryness. The desired product was isolated using column chromatography (EtOAc:MeOH:NH$_4$OH=70:28:2) to give Compound 50 (diastereoisomeric mixture in ratio 1:1, 0.160 g, 53% yield) as a white solid.

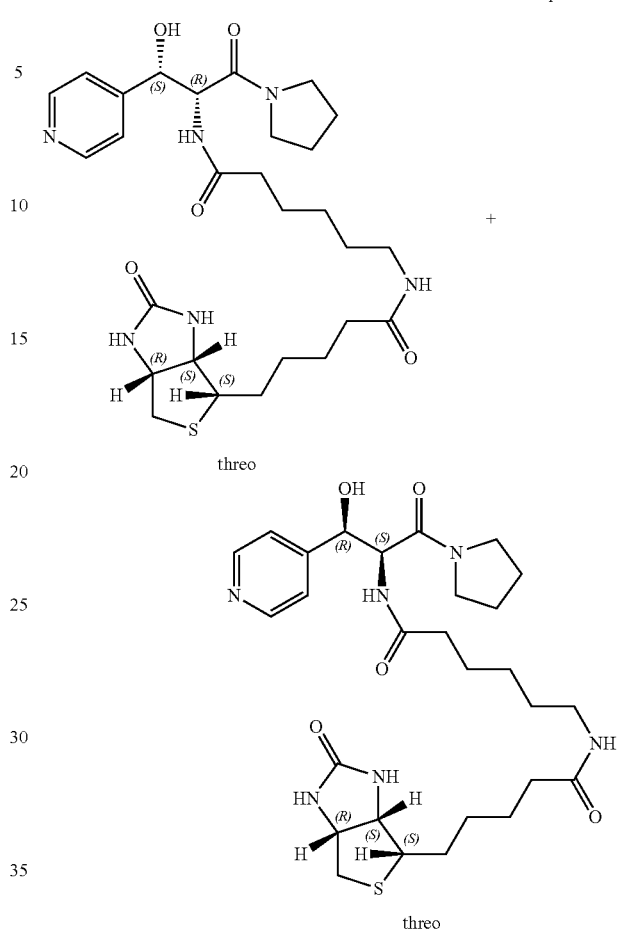

Compound 50 threo threo

MW: 574.74; Yield: 53%; White Solid; Mp (° C.): 64.3.

$R_f$: 0.2 (EtOAc:MeOH:NH$_4$OH=70:28:2).

$^1$H-NMR (CDCl$_3$,.): 1.17-1.32 (m, 2H), 1.40-1.60 (m, 4H), 1.60-1.90 (m, 6H), 1.90-2.10 (m, 4H), 2.15-2.30 (m, 4H), 2.74 (d, 1H, J=12.6 Hz), 2.91 (dd, J=4.8 Hz, 12.8 Hz), 2.95-3.10 (m, 1H), 3.10-3.45 (m, 4H), 3.60-3.72 (m, 1H), 4.34 (dd, 1H J=4.4 Hz J=7.5 Hz), 4.50-4.58 (m, 1H), 4.85-4.95 (m, 1H), 5.02-5.08 (m, 1H), 6.12 (s, 1H), 6.50-6.15 (m, 1H), 6.68 (s, 1H), 7.36 (m, 2H), 7.67 (q, 1H, J=8.12 Hz), 8.55 (d, 2H, J=5.8 Hz).

MS-ESI m/z (% rel. Int.): 575.3 ([MH]$^+$, 70).

HPLC: Method A, detection UV 254 nm, Compound 50 RT=3.61 min, peak area 97.2%.

Preparation of Compound 49.

trans-(4,5-Dihydro-5-(2-methoxypyridin-3-yl)oxazol-4-yl)(pyrrolidin-1-yl)methanone BAL 01014

BAL 01014 was prepared in accordance with method D using 2-methoxy-3-pyridinecarboxaldehyde (0.64 ml, 5.43 mmol), KOH (0.305 mg, 5.43 mmol) in methanol (5 mL) and 2-isocyano-1-(pyrrolidin-1-yl)ethanone BLE 04098 (0.75 g, 5.43 mmol). After work-up trans-(4,5-dihydro-5-(2-methoxypyridin-3-yl)oxazol-4-yl)(pyrrolidin-1-yl)methanone BAL 01014 was obtained (0.74 mg, 50% yield) as a white solid.

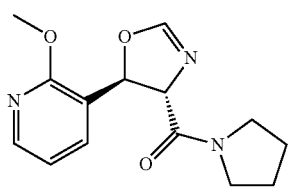

(+/−)

BAL 01014

MW: 275.30; Yield: 50%; White Solid; Mp (° C.): 110.1. R_f: 0.25 (EtOAc).

¹H NMR (CDCl₃,.): 1.82-2.10 (m, 4H, 2×CH₂), 3.40-3.62 (m, 3H, CH₂N), 3.80-3.90 (m, 3 H, CH₂N), 3.93 (s, 3H, OMe), 4.61 (dd, 1H, J=7 Hz, J=2 Hz, CH—N), 6.14 (d, 1H, J=7 Hz, CH—O), 6.90 (dd, 1H, J=7.3 Hz, J=5 Hz, ArH), 7.02 (d, 1H, J=2 Hz, OCH═N), 7.60 (dd, 1H, J=7.3 Hz, J=1.7 Hz, ArH), 8.13 (dd, 1H, J=5 Hz, J=1.8 Hz, ArH).

¹³C-NMR (CDCl₃,.): 24.3, 26.1, 46.3, 46.6, 53.5, 73.5, 78.1, 116.8, 122.2, 135.2, 146.5, 155.3, 160.5 and 167.4.

MS-ESI m/z (% rel. Int.): 276.1 ([MH]⁺, 42).

HPLC: Method A, detection UV 254 nm, BAL 01014 RT=3.63 min, peak area 97.2%.

3-(DL-threo-2-Amino-1-hydroxy-3-oxo-3-pyrrolidin-1-yl-propyl)-1H-pyridin-2-one hydrochloride Compound 49 trans-(4,5-Dihydro-5-(2-methoxypyridin-3-yl)oxazol-4-yl)(pyrrolidin-1-yl)methanone BAL 01014 (0.684 g, 2.487 mmol) was dissolved in methanol (10 mL). A solution of hydrochloric acid (37%, 0.6 mL) was added via syringe at RT. The mixture was stirred for 22 h at reflux. The residue was concentrated, triturated with EtOAc and filtered to obtain a yellow pale solid 3-(DL-threo-2-amino-1-hydroxy-3-oxo-3-pyrrolidin-1-yl-propyl)-1H-pyridin-2-one hydrochloride Compound 49 (136 mg, 19.0% yield).

Compound 49

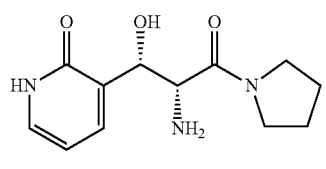

(±) HCl

MW: 287.74; Yield: 19.0%; Yellow Pale Solid; Mp (° C.): 180.

¹H NMR (CD₃OD,.): 1.82-2.09 (m, 4H, CH₂), 3.35-3.80 (m, 4H, CH₂N), 4.63 (s, 1H, CH—N), 5.17 (s, 1H, CH—O), 6.56 (t, 1H, ArH)), 7.5 (d, 1H, J=6.1 Hz, ArH), 7.86 (d, 1H, J=6.5 Hz, ArH).

¹³C-NMR (CD₃OD,.): 24.2, 26.0, 46.6, 46.6, 75.8, 79.7, 127.3, 127.5, 127.9, 129.4, 130.0, 132.3, 133.2, 148.1, 148.4, 155.3, 166.2.

MS-ESI m/z (% rel. Int.): 252.1 ([MH]⁺, 18), 163.0 (100).

HPLC: Method A, detection UV 254 nm, Compound 49 RT=1.13 min, peak area 84.0%.

Preparation of Compound 300.

(±)-threo-2-Phthalimide-3-hydroxy-3-(pyridin-4-yl)-1-(pyrrolidin-1-yl)propan-1-one hydrochloride Compound 300

(±)-threo-2-Amino-3-hydroxy-3-(pyridin-4-yl)-1-(pyrrolidin-1-yl)propan-1-one dihydrochloride Compound 22 (0.51 g, 1.64 mmol) was treated by 20 mL of a 1 N aqueous solution of K₂CO₃ and extracted (5×40 mL) with a mixture CH₂Cl₂:MeOH=90:10. The solution was dried over MgSO₄, filtered and evaporated to obtain the free base of Compound 22 (0.323 g, 82.5% yield) as a white solid.

In a 10 mL round-bottom flask phtalic anhydride (0.203 mg, 1.373 mmol) was added to the free base of Compound 22 (0.323 g, 1.37 mmol) and the mixture was heated from 65° C. to 145° C. and stirred 5 min at 145° C. After cooling a yellow black gum was obtained as a crude product. This crude product was purified by column chromatography (SiO₂, EtOAc: MeOH=100:0 to 90:10). After evaporation of the solvents, a white solid (±)-threo-2-phthalimide-3-hydroxy-3-(pyridin-4-yl)-1-(pyrrolidin-1-yl)propan-1-one BLE 04156A was obtained as a white solid (0.15 g, 30% yield). To (±)-threo-2-phthalimide-3-hydroxy-3-(pyridin-4-yl)-1-(pyrrolidin-1-yl)propan-1-one BLE 04156A (0.135 g, 0.37 mmol) was added a solution 0.1 N of HCl in isopropanol (10 mL) and the mixture was evaporated to dryness at 28° C. on a rotavapor then to high vacuum pump. (±)-threo-2-Phthalimide-3-hydroxy-3-(pyridin-4-yl)-1-(pyrrolidin-1-yl)propan-1-one hydrochloride Compound 300 (0.147 g, 24.5% yield) was obtained as a white solid.

Compound 300

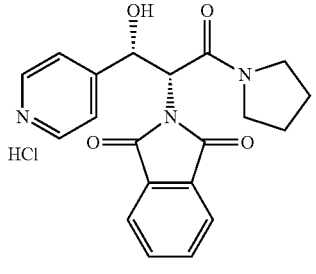

(±)

MW: 401.84; Yield: 24.5%; White Solid; Mp (° C.): 201.8

¹H-NMR (CD₃OD,): 1.60-1.90 (m, 4H, 2×CH₂), 2.95-3.09 (m, 1H, CH₂N), 3.30-3.47 (m, 3H, CH₂N), 5.30 (d, 1H, J=7.9 Hz, CH), 5.82 (d, 1H, J=7.9 Hz, CH), 7.80 (m, 4H, ArH), 8.25 (d, 2H, J=5.4 Hz, ArH), 8.81 (d, 2H, J=5.2 Hz, ArH).

¹³C-NMR (CD₃OD,): 24.7, 27.1, 47.7, 47.8, 58.0, 70.6, 124.8 (2×C), 127.5 (2×C), 132.6 (2×C), 136.1 (2×C), 142.5 (2×C), 164.9, 166.5, 168.8.

MS-ESI m/z (% rel. Int.): 366.0 ([MH]⁺, 22), 219.1 (100), 148.0 (47).

HPLC: Method A, detection UV 254 nm, RT=3.88 min, peak area 98.7%.

Preparation of Compound 301.

tert-butyl 5-((±)-threo-1-hydroxy-3-oxo-1-(pyridin-4-yl)-3-(pyrrolidin-1-yl)propan-2-ylcarbamoyl)pentylcarbamate Compound 237

To a solution of N-Boc-aminohexanoic acid (342 mg, 1.48 mmol) in THF (10 mL) was added N-methylmorpholine (163

L, 1.48 mmol). The solution was stirred for 5 min, cooled at −15° C. and treated dropwise with isobutyl chloroformate (211 L, 1.48 mmol). This solution was added via a stainless steal cannula to a solution of (±)-threo-2-amino-3-hydroxy-3-(pyridin-4-yl)-1-(pyrrolidin-1-yl)propan-1-one dihydrochloride Compound 22 (500 mg, 1.48 mmol) and N-methylmorpholine (489 mg, 1.47 mmol) in THF (10 mL) at −15° C. The reaction mixture was kept for 0.5 h at −15° C. followed by 2 h at 25° C. with continuous stirring. After evaporation of the solvent, the residue was partitioned between EtOAc and H₂O, washed with NaH₂PO₄, saturated aqueous NaHCO₃, dried over sodium sulfate and purified by column chromatography (SiO₂) with a gradient of 0% to 10% [v/v] MeOH in EtOAc to give tert-butyl 5-((±)-threo-1-hydroxy-3-oxo-1-(pyridin-4-yl)-3-(pyrrolidin-1-yl)propan-2-ylcarbamoyl)pentylcarbamate Compound 237 (455 mg, 69% yield) as a white solid.

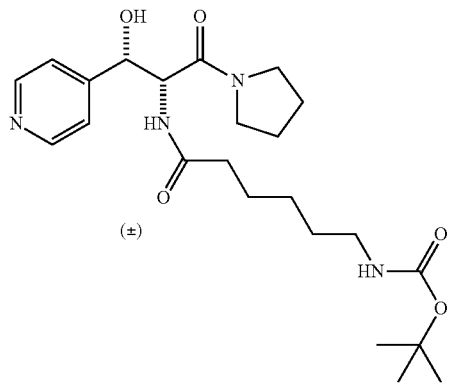

Compound 237

MW: 448.6; Yield: 69%; White Solid.
$R_f$: 0.20 (EtOAc:MeOH=90: 10).
¹H-NMR (CD₃OD,): 1.05-1.15 (m, 2H, CH₂), 1.35-1.55 (m, 13H, 2×CH₂+C(CH₃)₃), 1.75-1.95 (m, 4H, 2×CH₂), 2.00-2.20 (m, 2H, O=CCH₂), 3.05 (q, 2H, J=6.7 Hz, N—CH₂), 3.20-3.35 (m, 1H, N—CH), 3.38-3.50 (m, 2H, N—CH₂), 3.65-3.75 (m, 1H, N—CH), 4.72 (bs, 1H, NH), 4.98 (dd, 1H, J=8.8 Hz, J=3.6 Hz), 5.08 (d, 1H, J=3.3 Hz, OCH), 5.23 (bs, 1H, OH), 6.50 (d, 1H, J=8.7 Hz, NH), 7.35 (d, 2H, J=6.0 Hz, ArH), 8.58 (d, 2H, J=4.6 Hz, J=1.4 Hz, ArH).
MS-ESI m/z (% rel. Int.): 449.2 ([MH]⁺, 30), 349.2 (100).
HPLC: Method A, detection at 254 nm, RT=4.03 min, peak area 99.9%.

6-Amino-N-((±)-threo-1-hydroxy-3-oxo-1-(pyridin-4-yl)-3-(pyrrolidin-1-yl)propan-2-yl)hexanamide Compound 238

To a solution of tert-butyl 5-((±)-threo-1-hydroxy-3-oxo-1-(pyridin-4-yl)-3-(pyrrolidin-1-yl)propan-2-ylcarbamoyl) pentylcarbamate Compound 237 (81 mg, 0.181 mmol) in CH₂Cl₂ (8 mL) was added TFA (2 mL) at 0° C. and stirred for 2 h at 0° C. All the volatiles were evaporated to give a residue that was treated with a suspension of Amberlite-400 (OH⁻) in MeOH. After filtration, the filtrate was evaporated and the product was isolated by column chromatography (SiO₂) with CH₂Cl₂:MeOH:NH₄OH=10:5:0.4 to afford 6-amino-N-((±)-threo-1-hydroxy-3-oxo-1-(pyridin-4-yl)-3-(pyrrolidin-1-yl) propan-2-yl)hexanamide Compound 238 (40 mg, 64% yield) as a white solid.

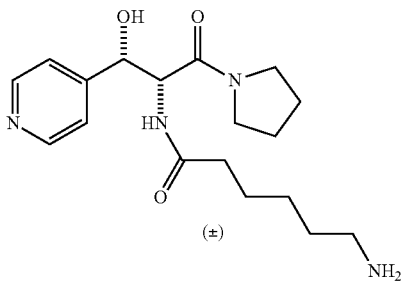

Compound 238

MW: 448.6; Yield: 64%; White Solid; Mp (° C.): 134.4
$R_f$: 0.30 (CH₂Cl₂:MeOH:NH₄OH=10:5:0.4).
¹H NMR (CDCl₃,): 1.12-1.30 (m, 2H, CH₂), 1.30-1.50 (m, 2H, CH₂), 1.50-1.65 (m, 2H, CH₂), 1.65-1.95 (m, 4H, CH₂), 2.10-2.30 (m, 2H, CH₂), 2.55-2.70 (t, 2H, J=6.9 Hz, CH₂), 3.10-3.20 (m, 2H, CH₂), 3.28-3.50 (m, 2H, CH₂), 3.60-3.70 (m, 1H, CH), 4.95 (dd, 1H, J=5.1 Hz, J=8.4 Hz, O—CH), 5.02 (d, 1H, J=5.0 Hz, OH), 7.11 Hz (d, J=8.48 Hz, 1H, ArH), 7.35 (dd, 2H, J=4.4 Hz, J=1.5 Hz, ArH), 8.55 (dd, J=1.5 Hz, J=4.6 Hz, 2H, ArH).
¹³C NMR (CDCl₃,): 24.0, 25.1, 25.8, 25.9, 32.5, 35.8, 41.7, 46.0, 46.9, 55.6, 72.6, 121.3 (2×C), 149.2, 149.5 (2×C), 168.9, 173.7.

(±)-threo-{3-[3-(3-{5-[1-(Hydroxy-pyridin-4-yl-methyl)-2-oxo-2-pyrrolidin-1-yl-ethylcarbamoyl]-pentylcarbamoyl}-propylcarbamoyl)-propylcarbamoyl]-propyl}-carbamic acid tert-butyl ester TTA 08156

Boc-GABA-GABA-GABA-OH (354 mg, 0.95 mmol) was stirred in CHCl₃ (40 mL) with Et₃N (0.3 mL, 2.1 mmol) and HOBT (145 mg, 1.05 mmol) at 4° C. for 5 min under nitrogen. EDC (205 mg, 1.05 mmol) was added and the mixture was stirred for 15 min at 4° C. 6-Amino-N-((±)-threo-1-hydroxy-3-oxo-1-(pyridin-4-yl)-3-(pyrrolidin-1-yl)propan-2-yl)hexanamide (333 mg, 0.95 mmol) in CHCl₃ (20 mL) was added dropwise and the mixture was stirred at 4° C. for 2 h and 15 h at RT under nitrogen. Brine (30 mL) was added and the product was extracted by CH₂Cl₂ (200 mL). The organic layer was washed with a solution of 2 N NaOH, brine and dried over MgSO₄. After filtration the solution was evaporated and dried to give a crude yellow oil (420 mg). After purification by column chromatography (SiO₂, CH₂Cl₂:MeOH=85:15) (±)-threo-{3-[3-(3-{5-[1-(hydroxy-pyridin-4-yl-methyl)-2-oxo-2-pyrrolidin-1-yl-ethylcarbamoyl]-pentylcarbamoyl}-propylcarbamoyl)-propylcarbamoyl]-propyl}-carbamic acid tert-butyl ester TTA 08156 (260 mg, 39% yield) was obtained as a pale yellow oil.

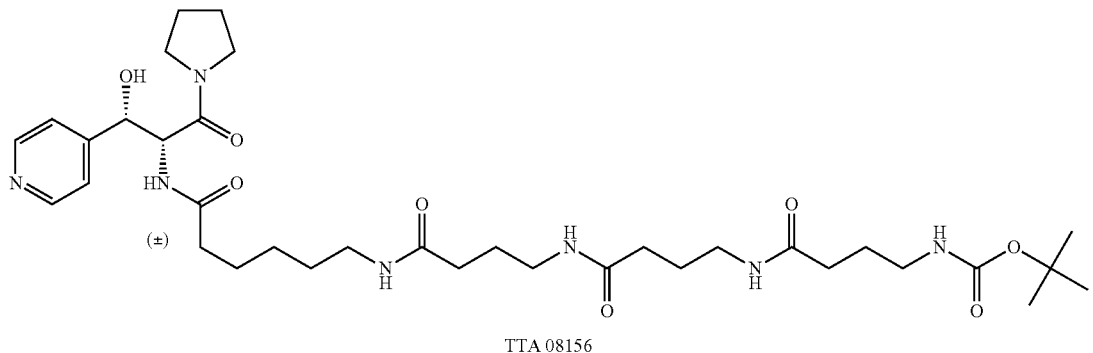 [SMILES: CC(C)(C)OC(=O)NCCCC(=O)NCCCC(=O)NCCCC(=O)NCCCCCC(=O)N[C@@H](C(=O)N1CCCC1)[C@@H](O)c1ccncc1]

TTA 08156

MW: 703.87; Yield: 39%; Pale Yellow Oil.
$R_f$: 0.20 (CH$_2$Cl$_2$:MeOH=9:1).
$^1$H-NMR (CDCl$_3$,): 1.17-1.25 (m, 2H, CH$_2$), 1.40-1.56 (m, 13H, 2×CH$_2$, 3×CH$_3$) 1.73-1.85 (m, 10H, 5×CH$_2$), 2.13-2.29 (m, 8H, 4×CH$_2$CO), 2.40 (s, 1H, OH), 3.09-3.67 (m, 12H, 6×CH$_2$—N), 4.91 (dd, 1H, J=4.9 Hz, J=8.5 Hz, CH—N), 5.05 (d, 1H, J=5.1 Hz, CH—O), 5.15 (t, 1H, J=5.8 Hz, NH), 7.01-7.04 (m, 1H, NH), 7.14 (t, 1H, J=5.6 Hz, NH), 7.33 (t, 1H, J=5.6 Hz, NH), 7.37 (d, 2H, J=6.0 Hz, ArH), 8.55 (d, 2H, J=6.0 Hz, ArH).
$^{13}$C-NMR (CD$_3$OD,): 24.0, 24.9, 25.6, 25.8, 26.1, 26.5, 28.4 (3×C), 29.0, 33.5, 33.7, 35.8, 38.6, 38.8, 39.1, 39.6, 46.1, 46.8, 55.6, 72.7, 79.5, 121.5 (×2), 149.1, 149.5 (×2), 156.7, 168.8, 173.1, 173.3, 173.4, 173.5.
MS-ESI m/z (% rel. Int.): 704.3 ([MH]$^+$, 100).
HPLC: Method A, detection UV 254 nm, TTA 08156 RT=3.90 min, peak area 99.0%.

6-(5-((3aR,6S,6aS)-hexahydro-2-oxo-1H-thieno[3,4-d]imidazol-6-yl)-pentanoylamino)-butyrylamino-butyrylamino-butyrylamino-N-((1R,2S)- & (1S,2R)-1-hydroxy-3-oxo-1-(pyridin-4-yl)-3-(pyrrolidin-1-yl)propan-2-yl)hexanamides Compound 301

(±)-threo-{3-[3-(3-{5-[1-(Hydroxy-pyridin-4-yl-methyl)-2-oxo-2-pyrrolidin-1-yl-ethylcarbamoyl]-pentylcarbamoyl}-propylcarbamoyl)-propylcarbamoyl]-propyl}-carbamic acid tert-butyl ester TTA 08156 (260 mg, 0.37 mmol) was stirred in MeOH (5 mL) with HCl 37% (0.3 mL, 3.70 mmol) for 15 min at 40° C. MeOH was evaporated and the residue was dried in vacuum. Amberlite IRA-400 (Cl$^-$) (6 mL, 8.4 mmol) was washed successively with water (2×10 mL), NaOH 0.5 N (3×20 mL), water (2×10 mL) and MeOH (3×10 mL). The previously obtained residue and washed Amberlite were stirred in MeOH (30 mL) for 5 min at RT. After filtration, the MeOH was evaporated to give amine in the free base form (210 mg, 94% yield). Biotin (95 mg, 0.38 mmole) was dissolved in a mixture CHCl$_3$/DMF (40 mL/10 mL) and Et$_3$N (0.11 mL, 0.77 mmol), HOBT (53 mg, 0.38 mmol) and EDC (75 mg, 0.38 mmol) were added and the solution stirred at RT for 2 h under nitrogen. The previously obtained amine (210 mg, 0.35 mmol) in CHCl$_3$ (10 mL) was added dropwise and the mixture was stirred for 24 h at RT under nitrogen. Brine (40 mL), 2 N NaOH (10 mL), CHCl$_3$ (50 mL) were added and the product was extracted by 3 additional extractions of a mixture CHCl$_3$/DMF (50 mL/10 mL). The combined organic layer was washed with brine, dried over MgSO$_4$, filtered, evaporated to give crude yellow oil (160 mg, 52% yield). The crude oil was purified by column chromatography (SiO$_2$, CH$_2$Cl$_2$:MeOH:NH$_3$=95:5:0.1 to 85:15:0.3) to obtain after evaporation 6-(5-((3aR,6S,6aS)-hexahydro-2-oxo-1H-thieno[3,4-d]imidazol-6-yl)-pentanoylamino)-butyrylamino-butyrylamino-butyrylamino-N-((1R,2S)- & (1S,2R)-1-hydroxy-3-oxo-1-(pyridin-4-yl)-3-(pyrrolidin-1-yl)propan-2-yl)hexanamides (diastereoisomeric mixture ratio 1:1) as a pale yellow oil (45 mg, 15% yield).

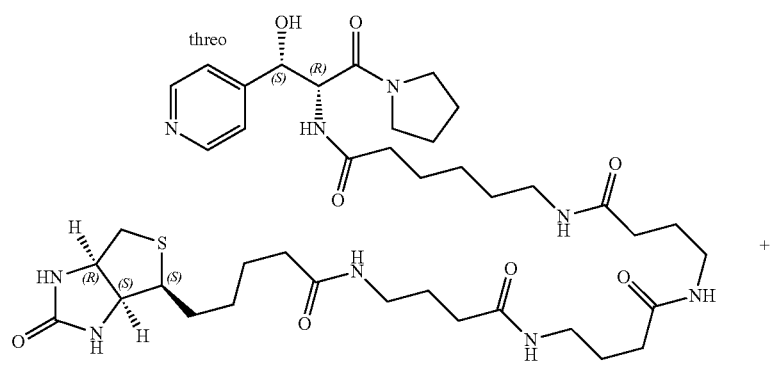

Compound 301

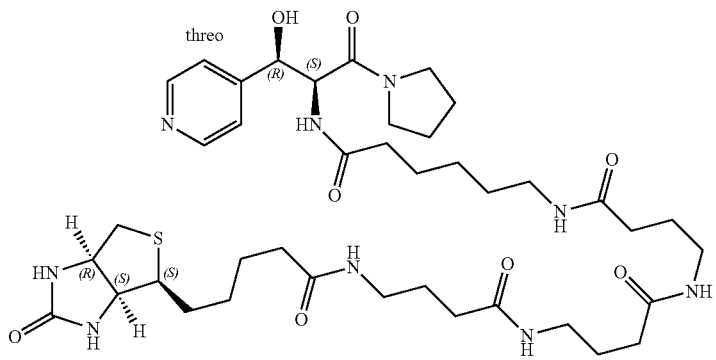

MW: 830.05; Yield: 15%; Pale Yellow Oil.

R$_f$: 0.30 (CH$_2$Cl$_2$:MeOH:NH$_3$=85:15:0.3).

$^1$H-NMR (CD$_3$OD,): 1.26-1.82 (m, 22H, 11×CH$_2$), 2.18-2.25 (m, 10H, 5×CH$_2$CO), 2.70 (d, 1H, J=12.7 Hz, CH$_2$—S), 2.92 (dd, 1H, J=4.8 Hz, J=12.7 Hz, CH$_2$S), 3.06-3.80 (m, 13H, 6×CH$_2$—N, CH—S), 4.29 (dd, 1H, J=4.4 Hz, J=7.8 Hz, CH—N), 4.48 (dd, 1H, J=4.9 Hz, J=7.8 Hz, CH—N), 4.82 (d, 1H, J=6.4 Hz, CH—N), 5.01 (d, 1H, J=6.4 Hz, CH—O), 7.49 (d, 2H, J=5.5 Hz, ArH), 8.5 (d, 2H, J=4.6 Hz, ArH).

$^{13}$C-NMR (CD$_3$OD,): 25.0, 26.5, 26.8, (2×C), 26.9 (2×C), 27.5, 29.5, 29.8, 30.1, 34.3, 34.4 (2×C), 36.4, 36.8, 39.8, 39.9, 40.1, 41.1, 47.2, 47.3, 57.1, 58.3, 61.6, 63.4, 73.1, 74.2, 123.5 (2×C), 149.9 (2×C), 152.8, 166.1, 170.0-175.3, 175.4 (2×C), 176.0, 176.1.

MS-ESI m/z (% rel. Int.): 830.2. ([MH]$^+$, 85), 219.1 (100).

HPLC: Method A, detection UV 254 nm, RT=3.70 min, peak area 99.8%.

Preparation of compound 302

(±)-threo-2-Amino-3-hydroxy-3-(piperidin-4-yl)-1-(pyrrolidin-1-yl)propan-1-one dihydrochloride Compound 302

(±)-threo-2-Amino-3-hydroxy-3-(pyridin-4-yl)-1-(pyrrolidin-1-yl)propan-1-one dihydrochloride Compound 22 (500 mg, 1.61 mmol) was stirred in AcOH (10 mL) with PtO$_2$ hydrate typical (Pt content 79-84%, 100 mg) under hydrogen at atmospheric pressure for 24 h at RT. After filtration on Celite® 545, the filtrate was evaporated and the residue was dried under vacuum to give a beige solid (450 mg, 88.2% yield). The crude product was stirred in MeOH (50 mL) with Amberlite (Cl—) IRA-400 (9 mL, 12.7 mmol washed beforehand by NaOH 0.5 N then water and MeOH) at RT for 15 min. The mixture was filtered off, the filtrate was evaporated and the free base form was purified by column chromatography (SiO$_2$, CH$_2$Cl$_2$:MeOH:20% NH$_3$ in H$_2$O=70:30:8) to give (±)-threo-2-amino-3-hydroxy-3-(piperidin-4-yl)-1-(pyrrolidin-1-yl)propan-1-one TTA 08144A (226 mg, 58% yield). HCl Treatment in MeOH gave (±)-threo-2-amino-3-hydroxy-3-(piperidin-4-yl)-1-(pyrrolidin-1-yl)propan-1-one dihydrochloride Compound 302 (190 mg, 28% yield) as a white solid.

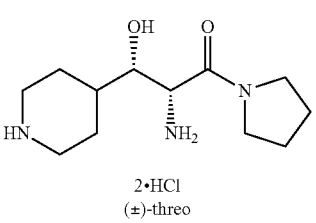

Compound 302

2·HCl
(±)-threo

MW: 314.25; Yield: 28.0%; White Solid; Mp (° C.): 197.5

R$_f$: 0.20 (CH$_2$Cl$_2$:MeOH:20% NH$_3$ in H$_2$O=70:30:8, free base).

$^1$H-NMR (CD$_3$OD,): 1.57-2.00 (m, 9H, 4×CH$_2$& CH), 2.94-3.08 (m, 2H, CH$_2$—N), 3.46-3.77 (m, 7H, 3×CH$_2$—N, CH—N), 4.33 (s, 1H, CH—O).

$^{13}$C-NMR (CD$_3$OD,): 22.5, 23.4, 24.1, 24.7, 35.2, 42.2, 42.5, 45.4, 45.5, 52.0, 69.8, 164.6.

MS-ESI m/z (% rel. Int.): 242.2 ([MH]$^+$, 45), 129.1 (100).

HPLC: Method A, detection UV 214 nm, RT=0.70 min, peak area 98.0%.

Preparation of Compound 70

Method D (in CH$_2$Cl$_2$):

To a stirred solution of DL-threo-2-amino-3-hydroxy-3-(pyridin-4-yl)-1-(pyrrolidin-1-yl)propan-1-one dihydrochloride Compound 22 (0.15 g, 0.49 mmol) in 10 mL of CH$_2$Cl$_2$ at +4° C. were added triethylamine (200 µl, 1.45 mmol) and very slowly acid chloride in 3 mL of CH$_2$Cl$_2$. The mixture was stirred overnight at RT under nitrogen and then partitioned between CH$_2$Cl$_2$ and 1 N aqueous sodium carbonate. The organic layer was evaporated and the obtained residue purified by column chromatography on silica (EtOAc:MeOH=95:5). The hydrochloride salt was obtained in MeOH at 0° C. with 0.3 M HCl in diethylether to give after evaporation of solvents and drying the acylated compound.

Benzyl DL-threo-3-hydroxy-1-oxo-3-(pyridin-4-yl)-1-(pyrrolidin-1-yl)propan-2-ylcarbamate hydrochloride Compound 58

The compound was prepared according to method D with benzyl chloroformate (91 mg, 0.53 mmol). After work-up benzyl DL-threo-3-hydroxy-1-oxo-3-(pyridin-4-yl)-1-(pyrrolidin-1-yl)propan-2-ylcarbamate hydrochloride Compound 58 was obtained as a white solid (90 mg, 46% yield).

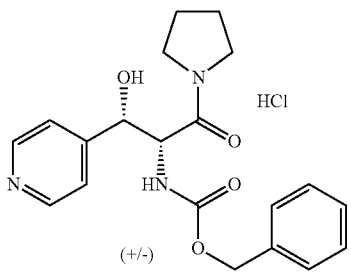

Compound 58

(+/-)

MW: 405.9; Yield: 46.0%; White Solid; Mp (° C.): 185.3. $R_f$: 0.38 (MeOH:EtOAc=10:90) free base.

$^1$H-NMR (CD$_3$OD,.): 1.87-2.03 (m, 4H, 2×CH$_2$), 3.40-3.48 (m, 2H, CH$_2$N), 3.56-3.62 (m, 2H, CH$_2$N), 4.85-5.04 (m, 3H, CH$_2$O, CHO), 5.39 (d, 1H, J=2.8 Hz, NH), 7.26-7.36 (m, 5H, ArH), 8.12 (d, 2H, J=6.0 Hz, ArH), 8.69 (d, 2H, J=6.0 Hz, ArH).

$^{13}$C-NMR (CD$_3$OD,.): 25.0, 27.0, 47.5, 48.0, 58.8, 67.9, 72.7, 126.6 (2×C), 129.1, 129.2, 129.5, 138.1, 141.9 (2×C), 158.1, 164.4, 169.2.

MS-ESI m/z (% rel. Int.): 370.1 ([MH]$^+$, 15), 219.0 (100).

HPLC: Method A, detection UV 254 nm, Compound 58 RT=4.10 min, peak area 99.8%.

trans-3-Methyl-5-pyridin-4-yl-4-(pyrrolidine-1-carbonyl)-oxazolidin-2-one hydrochloride
Compound 70

To a stirred solution of DL-threo-3-hydroxy-1-oxo-3-(pyridin-4-yl)-1-(pyrrolidin-1-yl)propan-2-ylcarbamate Compound 58 free base (0.10 g, 0.27 mmol) in a mixture of DMSO:DMF (2 mL:0.2 mL) at 6° C. were added slowly tert-BuOK (38 mg, 0.33 mmol) and dimethyl sulfate (26 µL, 0.27 mmol). The mixture was stirred 15 h at RT under nitrogen and partitioned between ice water (5 mL), 1M Na$_2$CO$_3$ (2 mL) and ethyl acetate (100 mL). The organic phase was washed with brine (20 mL) and dried over MgSO$_4$. After removing ethyl acetate by evaporation, the crude product was dried to give the crude free base as an oil. The hydrochloride salt was obtained in MeOH at 0° C. using a 0.3 M solution of HCl in diethylether. After precipitation in diethylether, trans-3-methyl-5-pyridin-4-yl-4-(pyrrolidine-1-carbonyl)-oxazolidin-2-one hydrochloride was obtained as a pale yellow solid (80 mg, 95% yield). A further crystallization in EtOAc:MeOH (10:1) gave Compound 70 as a white solid (16 mg, 20% yield).

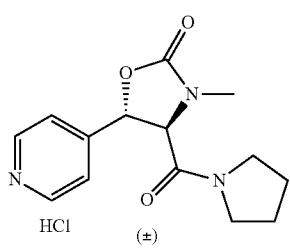

Compound 70

(±)

MW: 311.76; Yield: 20%; White Solid; Mp (° C.): 168.6. $R_f$: 0.15 (EtOAc:MeOH=95:5), free base.

$^1$H-NMR (CD$_3$OD,): 1.90-2.10 (m, 4H, 2×CH$_2$), 2.84 (s, 3H, CH$_3$), 3.47-3.70 (m, 4H, CH$_2$N), 4.82 (m, 1H, CH), 5.89 (m, 1H, CH), 8.17 (m, 2H, ArH), 8.97 (m, 2H, ArH).

$^{13}$C-NMR (CD$_3$OD,): 24.9, 27.1, 30.2, 48.1, 64.9, 76.3, 125.6 (2×C), 143.8 (2×C), 159.1, 160.1, 167.3.

MS-ESI m/z (% rel. Int.): 276.1 ([MH]$^+$, 25), 177.1 (100).

HPLC: Method A, detection UV 254 nm, Compound 70 RT=2.00 min, peak area 97.0%.

What is claimed is:

1. A compound of formula (i) or of (ii)

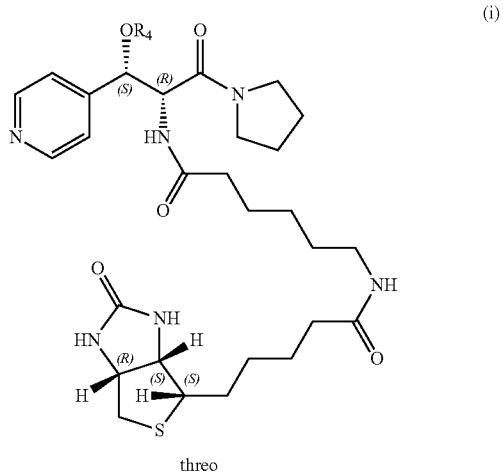

(i)

threo

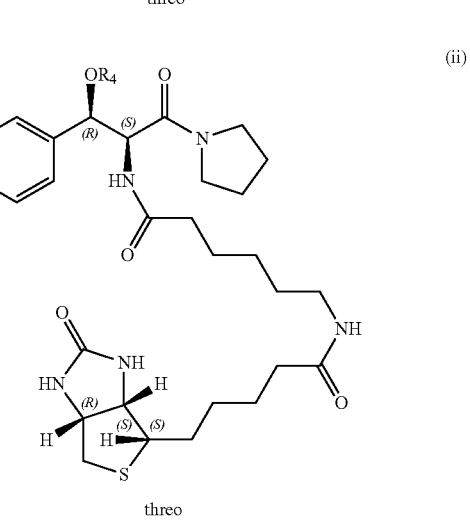

(ii)

threo where $R_4$ is H, alkyl of 1 to 6 carbons or CO—$R_5$ where $R_5$ is alkyl of 1 to 6 carbons, or a pharmaceutically acceptable salt of said compound.

2. A compound in accordance with claim 1 where $R_4$ is H.

3. A method of treating pain in a mammal in need of such treatment, comprising administering to said mammal the compound of claim 1 or a pharmaceutically acceptable salt thereof.

* * * * *